United States Patent
Teshigawara et al.

(10) Patent No.: US 12,307,673 B2
(45) Date of Patent: May 20, 2025

(54) NUCLEAR MEDICINE DIAGNOSIS APPARATUS, DATA PROCESSING METHOD, AND COMPUTER PROGRAM PRODUCT

(71) Applicant: CANON MEDICAL SYSTEMS CORPORATION, Tochigi (JP)

(72) Inventors: Manabu Teshigawara, Otawara (JP); Ryo Okuda, Utsunomiya (JP)

(73) Assignee: CANON MEDICAL SYSTEMS CORPORATION, Tochigi (JP)

(*) Notice: Subject to any disclaimer, the term of this patent is extended or adjusted under 35 U.S.C. 154(b) by 284 days.

(21) Appl. No.: 17/896,250

(22) Filed: Aug. 26, 2022

(65) Prior Publication Data

US 2023/0065542 A1    Mar. 2, 2023

(30) Foreign Application Priority Data

Aug. 26, 2021  (JP) ................................ 2021-138363

(51) Int. Cl.
| | | |
|---|---|---|
| G06T 7/00 | (2017.01) | |
| G06T 5/92 | (2024.01) | |
| G06V 10/22 | (2022.01) | |
| A61B 6/03 | (2006.01) | |
| A61B 6/46 | (2024.01) | |

(52) U.S. Cl.
CPC .............. *G06T 7/0016* (2013.01); *G06T 5/92* (2024.01); *G06V 10/235* (2022.01); *A61B 6/037* (2013.01);
(Continued)

(58) Field of Classification Search
CPC ........ G06T 7/0016; G06T 5/92; G06V 10/235
See application file for complete search history.

(56) References Cited

U.S. PATENT DOCUMENTS

| | | | |
|---|---|---|---|
| 7,024,024 B1* | 4/2006 | Aiazian .................. | A61B 8/481 382/128 |
| 2010/0067767 A1* | 3/2010 | Arakita .................. | A61B 6/504 382/131 |

(Continued)

FOREIGN PATENT DOCUMENTS

| | | |
|---|---|---|
| JP | 2006-145281 A | 6/2006 |
| JP | 2013-137303 A | 7/2013 |

(Continued)

OTHER PUBLICATIONS

"Cardiac Positron Emission Tomography: Overview of Myocardial Perfusion, Myocardial Blood Flow and Myocardial Blood Flow Reserve Imaging", Nov. 1, 2011, XP055112255, (Xiao-Bo Pan et al). (Year: 2011).*

(Continued)

*Primary Examiner* — Myron Wyche
(74) *Attorney, Agent, or Firm* — Oblon, McClelland, Maier & Neustadt, L.L.P.

(57) ABSTRACT

A nuclear medicine diagnosis apparatus according to an embodiment includes a processing circuit. The processing circuit is configured to obtain nuclear medicine data; to time-divide the nuclear medicine data into at least first nuclear medicine data and second nuclear medicine data; and to identify a biological accumulation region, on the basis of a temporal change in data values included in the first nuclear medicine data and the second nuclear medicine data.

8 Claims, 5 Drawing Sheets

(52) U.S. Cl.
CPC ............... *A61B 6/463* (2013.01); *A61B 6/469* (2013.01); *G06T 2207/10104* (2013.01); *G06T 2207/20092* (2013.01); *G06T 2207/30096* (2013.01); *G06V 2201/03* (2022.01)

(56) References Cited

U.S. PATENT DOCUMENTS

| | | |
|---|---|---|
| 2013/0134314 A1 | 5/2013 | Teshigawara et al. |
| 2018/0256127 A1 | 9/2018 | Matthews et al. |
| 2019/0150860 A1 | 5/2019 | Hamada et al. |
| 2021/0007697 A1 | 1/2021 | Matthews et al. |

FOREIGN PATENT DOCUMENTS

| | | | |
|---|---|---|---|
| JP | 2016-148629 A | 8/2016 | |
| WO | WO 2017/048904 A1 | 3/2017 | |
| WO | WO2017048904 | * 3/2017 | ............... G01T 1/29 |
| WO | WO 2017/179256 A1 | 10/2017 | |

OTHER PUBLICATIONS

Extended European Search Report issued Jan. 9, 2023 in European Patent Application No. 22192461.6, citing documents 1-4, 15, and 24 therein, 9 pages.

Xiao-Bo Pan, et al., "Cardiac Positron Emission Tomography: Overview of Myocardial Perfusion, Myocardial Blood Flow and Myocardial Flow Reserve Imaging," Siemens, Nov. 2011, XP055112255, 24 pages.

Office Action issued Mar. 11, 2025, in corresponding European Patent Application No. 22192461.6; 5 pages.

Office Action issued Mar. 12, 2025, in corresponding Japanese Patent Application No. 2021-138363, 4 pages.

* cited by examiner

NUCLEAR MEDICINE DIAGNOSIS APPARATUS, DATA PROCESSING METHOD, AND COMPUTER PROGRAM PRODUCT

CROSS-REFERENCE TO RELATED APPLICATIONS

This application is based upon and claims the benefit of priority from Japanese Patent Application No. 2021-138363, filed on Aug. 26, 2021; the entire contents of which are incorporated herein by reference.

FIELD

Embodiments described herein relate generally to a nuclear medicine diagnosis apparatus, a data processing method, and a computer program product.

BACKGROUND

Fluorodeoxyglucose (FDG)-Positron Emission Tomography (PET) images may exhibit biological FDG accumulation in addition to FDG accumulation caused by a tumor. In this regard, biological accumulation in the brain, the heart, the bladder, the tonsils, the ovary in the ovulation phase, or the endometrium can easily be determined because the positions and the forms thereof are relatively constant. In contrast, for example in the case of biological accumulation in the digestive system, particularly in the large intestine, there are some biological accumulation positions and forms of which vary among patients and which is time dependent. In those situations, image interpreters empirically judge whether each accumulation is tumor accumulation or biological accumulation.

In the biological accumulation judging process empirically performed by the image interpreters, it will be ideal when a nuclear medicine diagnosis apparatus is able to provide information that can assist accurate judgment.

DETAILED DESCRIPTION

A nuclear medicine diagnosis apparatus according to an embodiment includes a processing circuit. The processing circuit is configured to obtain nuclear medicine data; to time-divide the nuclear medicine data into at least first nuclear medicine data and second nuclear medicine data; and to identify a biological accumulation region, on the basis of a temporal change in data values included in the first nuclear medicine data and the second nuclear medicine data.

Exemplary embodiments of a nuclear medicine diagnosis apparatus, a data processing method, and a program will be explained in detail below, with reference to the accompanying drawings.

First Embodiment

Figure 1:
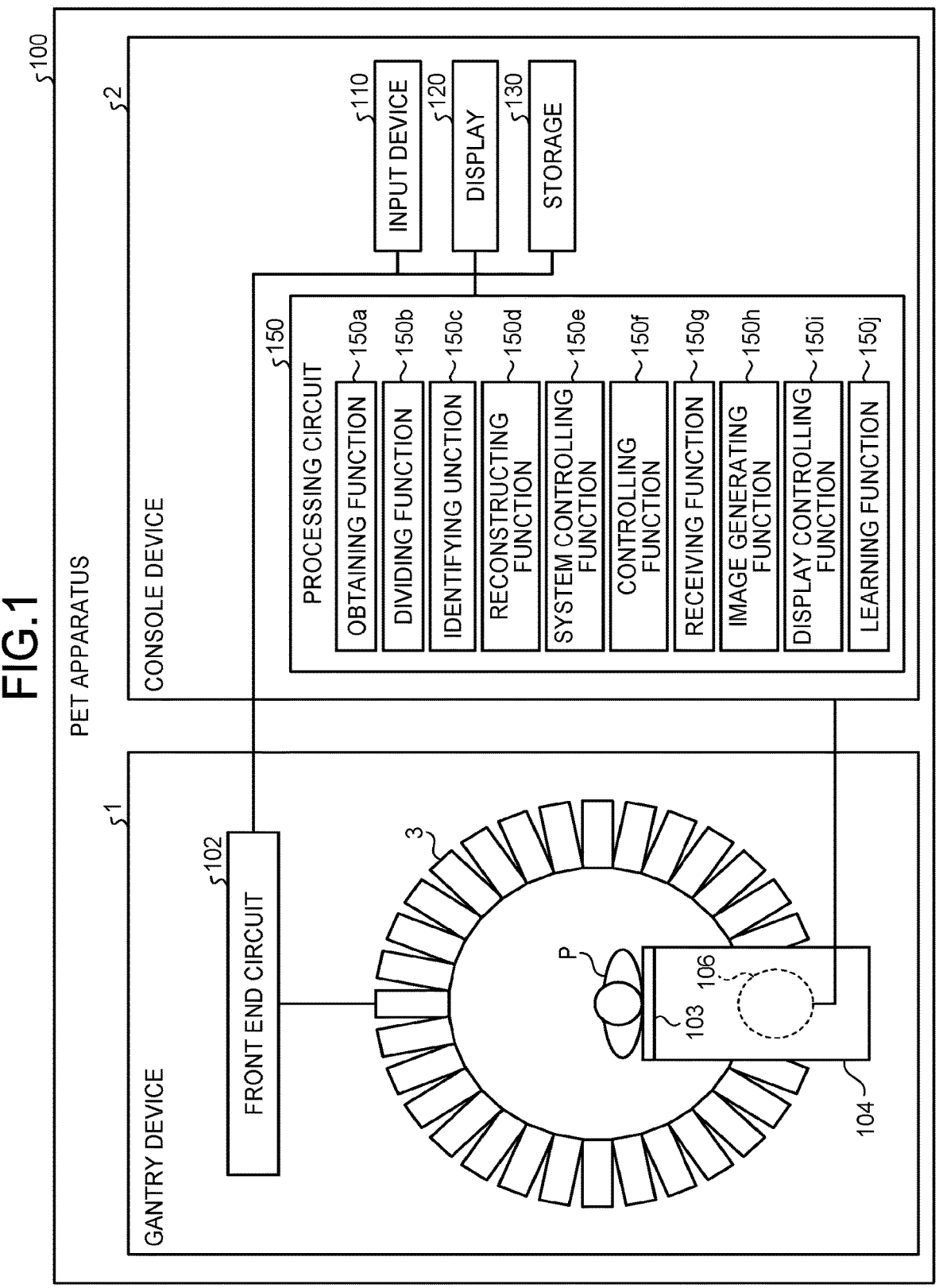
FIG. 1 is a diagram illustrating an example of a nuclear medicine diagnosis apparatus according to an embodiment.

FIG. 1 is a diagram illustrating a configuration of a PET apparatus 100 serving as a nuclear medicine diagnosis apparatus according to an embodiment. As illustrated in FIG. 1, the PET apparatus 100 according to the embodiment includes a gantry device 1 and a console device 2 serving as a medical image processing device. The gantry device 1 includes detectors 3, a front end circuit 102, a tabletop 103, a table 104, and a table driving unit 106.

The detectors 3 are detectors configured to detect radiation, by detecting scintillation photons (fluorescent light) representing light that is re-released when a substance in an excited state transitions back into a ground state as a result of an interaction between annihilation gamma rays and light emitting bodies (scintillators), the annihilation gamma rays being generated by positrons emitted from medical agent that is administered to a patient P and that is aggregated pair-annihilating with electrons of the surrounding tissues. The detectors 3 are configured to detect radiation energy information of the annihilation gamma rays, the annihilation gamma rays being generated by positrons emitted from medical agent that is administered to a patient P and that is aggregated pair-annihilating with electrons of the surrounding tissues. The plurality of detectors 3 are arranged so as to surround the patient P in a ring formation, while forming a plurality of detector blocks, for example.

An example of a specific configuration of the detectors 3 may be detectors of an Anger type using a photon counting method and including, for example, scintillators, optical detecting elements, and a light guide. In another example of the configuration, the detectors 3 may be non-Anger type detectors in which scintillators and optical detecting elements have one-to-one optical coupling. In other words, each of the pixels included in the detectors 3 has a scintillator and an optical detecting element configured to detect generated scintillation photons.

The scintillators are configured to convert the annihilation gamma rays into scintillation photons (or optical photons) and to output the scintillation photons, the annihilation gamma rays being generated by positrons emitted from medical agent that is administered to a patient P and that is aggregated pair-annihilating with electrons of the surrounding tissues. For example, the scintillators are formed with scintillator crystals such as those of Lutetium Yttrium Oxyorthosilicate (LYSO), Lutetium Oxyorthosilicate (LSO), Lutetium Gadolinium Oxyorthosilicate (LGSO), or Bismuth Germanium Oxide (BGO) and are arranged two-dimensionally, for example.

As the optical detecting elements, for example, Silicon Photomultipliers (SiPMs) or photomultiplier tubes may be used. Each of the photomultiplier tubes includes: a photocathode configured to receive the scintillation photons and to generate photoelectrons; multi-stage dynodes configured to provide an electric field for accelerating the generated photoelectrons; and an anode through which electrons flow out. The photomultiplier tubes are configured to multiply the photoelectrons derived from the scintillation photons output from the scintillators and to convert the multiplied photoelectrons into electrical signals.

Further, by employing the front end circuit 102, the gantry device 1 is configured to generate count information from output signals of the detectors 3 and to store the generated count information into a storage 130 of the console device 2. In this situation, the detectors 3 are divided into a plurality of blocks and are provided with the front end circuit 102.

The front end circuit 102 is configured to generate the count information based on the output signals from the detectors 3. The count information includes detection positions of the annihilation gamma rays, energy values, and detection times. For example, the front end circuit 102 is configured to identify a plurality of optical detecting elements that converts scintillation photons into electrical signals at mutually the same time. Further, the front end circuit 102 is configured to identify scintillator numbers (P) indicating the positions of the scintillators to which the annihilation gamma rays became incident. As for a means for identifying the positions of the scintillators to which the annihilation gamma rays became incident, it is possible to identify the positions by performing a center-of-gravity calculation on the basis of the positions of the optical detecting elements and intensities of the electrical signals. Further, when the element sizes of the scintillators and the optical detecting elements correspond with each other, the scintillators corresponding to the optical detecting elements from which outputs are obtained may be identified as the positions of the scintillators to which the annihilation gamma rays become incident.

Further, the front end circuit 102 is configured to identify energy values (E) of the annihilation gamma rays that become incident to the detectors 3, through an integral calculation on the intensities of the electrical signals output from the optical detecting elements. Further, the front end circuit 102 is configured to identify detection times (T) at which the scintillation photons from the annihilation gamma rays were detected by the detectors 3. The detection times (T) may be absolute times or elapsed time periods since the start of an imaging process. As explained herein, the front end circuit 102 is configured to generate the count information including the scintillator numbers (P), the energy values (E), and the detection times (T).

In this situation, the front end circuit 102 is realized by using, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The front end circuit 102 is an example of a front end unit.

The tabletop 103 is a bed on which the patient P is placed and is arranged over the table 104. The table driving unit 106 is configured to move the tabletop 103 under control of a controlling function 150f of a processing circuit 150. For example, the table driving unit 106 is configured to move the patient P to the inside of an imaging opening of the gantry device 1, by moving the tabletop 103.

Upon receipt of an operation performed by an operator on the PET apparatus 100, the console device 2 is configured to control imaging of a PET image and to reconstruct the PET image by using the count information acquired by the gantry device 1. As illustrated in FIG. 1, the console device 2 includes the processing circuit 150, an input device 110, a display 120, and the storage 130. In this situation, functional units included in the console device 2 are connected together via a bus. Details of the processing circuit 150 will be explained later.

The input device 110 is a mouse, a keyboard, and/or the like used by the operator of the PET apparatus 100 for inputting various types of instructions and various types of settings and is configured to transfer the input various types of instructions and various types of settings to the processing circuit 150. For example, the input device 110 may be used for inputting an instruction to start an imaging process.

The display 120 is a monitor or the like referenced by the operator and is configured, under control of the processing circuit 150, to display a respiratory waveform and the PET image of the patient and to display a Graphical User Interface (GUI) used for receiving the various types of instructions and the various types of settings from the operator.

The storage 130 is configured to store therein various types of data used in the PET apparatus 100. For example, the storage 130 is configured by using a memory and may be, in an example, realized by using a semiconductor memory element such as a Random Access Memory (RAM) or a flash memory, or a hard disk, an optical disk, or the like. The storage 130 is configured to store therein the count information which is the information in which the scintillator numbers (P), the energy values (E), and the detection times (T) are kept in correspondence with one another, coincidence information in which coincidence numbers serving as serial numbers of pieces of coincidence information are kept in correspondence with sets of count information, the reconstructed PET image, and the like.

The processing circuit 150 includes an obtaining function 150a, a dividing function 150b, an identifying function 150c, a reconstructing function 150d, a system controlling function 150e, the controlling function 150f, a receiving function 150g, an image generating function 150h, a display controlling function 150i, and a learning function 150j. The functions other than the system controlling function 150e will be explained in detail later.

In an embodiment, processing functions implemented by the obtaining function 150a, the dividing function 150b, the identifying function 150c, the reconstructing function 150d, the system controlling function 150e, the controlling function 150f, the receiving function 150g, the image generating function 150h, the display controlling function 150i, and the learning function 150j are stored in the storage 130 in the form of computer-executable programs. The processing circuit 150 is a processor configured to realize the functions corresponding to the programs by reading and executing the programs from the storage 130. In other words, the processing circuit 150 that has read the programs has the functions illustrated within the processing circuit 150 in FIG. 1.

Further, although the example is explained with reference to FIG. 1 in which the single processing circuit (i.e., the processing circuit 150) realizes the processing functions implemented by the obtaining function 150a, the dividing function 150b, the identifying function 150c, the reconstructing function 150d, the system controlling function 150e, the controlling function 150f, the receiving function 150g, the image generating function 150h, the display controlling function 150i, and the learning function 150j, it is also acceptable to structure the processing circuit 150 by combining together a plurality of independent processors so that the functions are realized as a result of the processors executing the programs. In other words, each of the above-mentioned functions may be structured as a program, so that the single processing circuit (i.e., the processing circuit 150)

executes the programs. In another example, one or more specific functions may be installed in a dedicated and independent program executing circuit.

The term "processor" used in the above explanations denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors are configured to realize the functions by reading and executing the programs saved in the storage 130.

In FIG. 1, the obtaining function 150a, the dividing function 150b, the identifying function 150c, the reconstructing function 150d, the system controlling function 150e, the controlling function 150f, the receiving function 150g, the image generating function 150h, the display controlling function 150i, and the learning function 150j are examples of an obtaining unit, a dividing unit, an identifying unit, a reconstructing unit, a system controlling unit, a controlling unit, a receiving unit, an image generating unit, a display controlling unit, and a learning unit, respectively.

By employing the system controlling function 150e, the processing circuit 150 is configured to control the entirety of the PET apparatus 100, by controlling the gantry device 1 and the console device 2. For example, by employing the system controlling unit 150e, the processing circuit 150 is configured to control imaging processes performed by the PET apparatus 100.

The processing circuit 150 is configured to control the table driving unit 106 by employing the controlling function 150f.

Next, a background of the embodiment will be briefly explained.

Fluorodeoxyglucose (FDG)-Positron Emission Tomography (PET) images may exhibit biological FDG accumulation in addition to FDG accumulation caused by a tumor. In this regard, biological accumulation in the brain, the heart, the bladder, the tonsils, the ovary in the ovulation phase, or the endometrium can easily be determined because the positions and the forms thereof are relatively the same. In contrast, positions and forms of certain biological accumulation (e.g., biological accumulation in the digestive system, particularly in the large intestine) vary among patients. In those situations, image interpreters empirically judge whether each accumulation is tumor accumulation or biological accumulation.

In the biological accumulation judging process empirically performed by the image interpreters, it will be ideal when the PET apparatus 100 is able to provide information that can assist accurate judgment.

In view of the background described above, the nuclear medicine diagnosis apparatus 100 according to the embodiment includes the processing circuit 150. The processing circuit 150 is configured to obtain nuclear medicine data by employing the obtaining function 150a, is configured to time-divide the nuclear medicine data into two or more sections that are to be separated into first nuclear medicine data and second nuclear medicine data by employing the dividing function 150b, and is configured to identify a biological accumulation region on the basis of a temporal change in data values included in the first nuclear medicine data and the second nuclear medicine data by employing the identifying function 150c.

Figure 2:
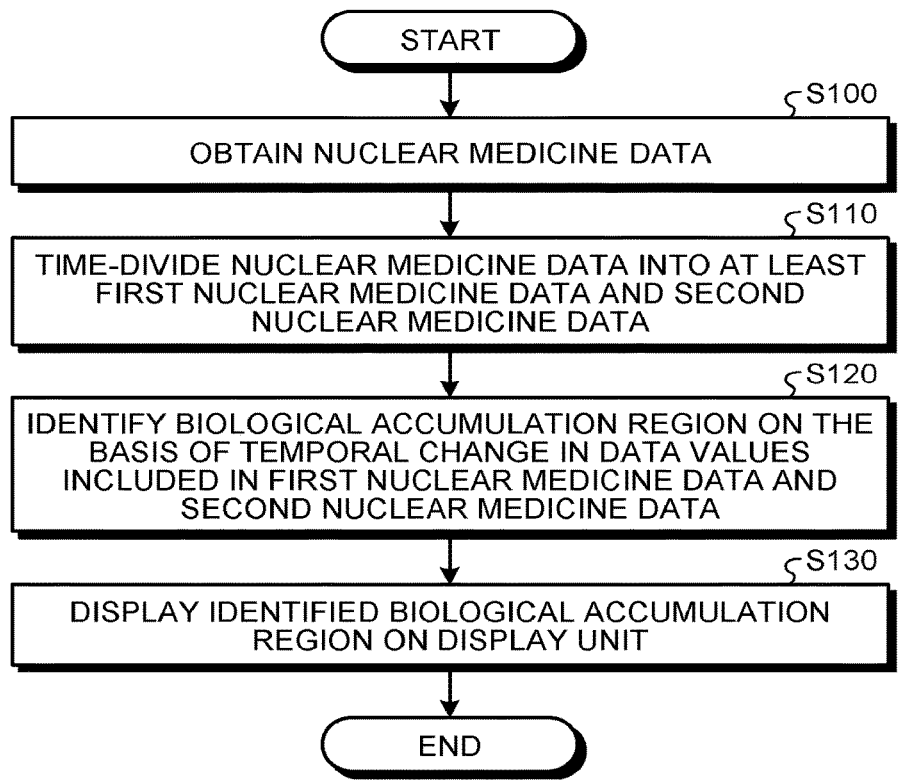
FIG. 2 is a flowchart for explaining a flow in a process performed a nuclear medicine diagnosis apparatus according to a first embodiment.

Next, these processes will be explained with reference to FIGS. 2 to 6. FIG. 2 is a flowchart for explaining a flow in a process performed by the nuclear medicine diagnosis apparatus according to the first embodiment.

To begin with, at step S100, by employing the obtaining function 150a, the processing circuit 150 obtains nuclear medicine data from the front end circuit 102. In this situation, the nuclear medicine data obtained from the front end circuit 102 by the processing circuit 150 while employing the obtaining function 150a may be, for example, raw data, i.e., the count information including the scintillator numbers (P), the energy values (E), and the detection times (T), for example.

In another example, the nuclear medicine data obtained by the processing circuit 150 while employing the obtaining function 150a may be a reconstructed image obtained by performing a reconstruction process on the count information represented by those pieces of raw data.

Figure 3:
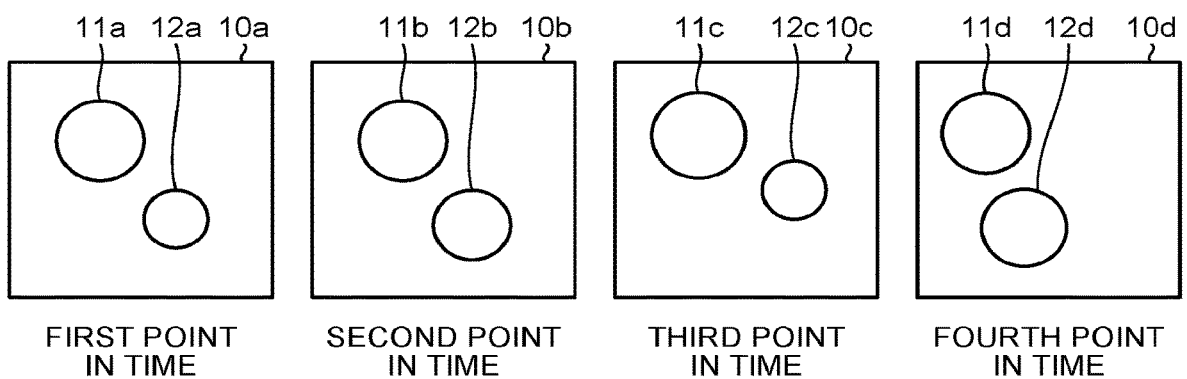
FIG. 3 is a drawing for explaining a process according to the embodiment.

Subsequently, at step S110, the processing circuit 150 time-divides the nuclear medicine data into at least two sections that are to be separated into the first nuclear medicine data and the second nuclear medicine data. This situation is illustrated in FIG. 3. In FIG. 3, nuclear medicine data 10a, 10b, 10c, and 10d represent pieces of nuclear medicine data corresponding to a first point in time, a second point in time, a third point in time, and a fourth point in time, respectively, obtained by performing the time-division process on a series of nuclear medicine data obtained by the processing circuit 150 while employing the obtaining function 150a. In the example in FIG. 3, for instance, the nuclear medicine data 10a and the nuclear medicine data 10b represent an example of the first nuclear medicine data, whereas the nuclear medicine data 10c and the nuclear medicine data 10d represent an example of the second nuclear medicine data. In another example, the nuclear medicine data 10a may be the first nuclear medicine data, while the nuclear medicine data 10b may be the second nuclear medicine data, for instance.

After that, at step S120, by employing the identifying function 150c, the processing circuit 150 identifies a biological accumulation region on the basis of temporal changes in data values included in the first nuclear medicine data and the second nuclear medicine data.

This process will be explained, with reference to FIGS. 3 to 5. The following will explain an example in FIG. 3 in which the nuclear medicine data 10a corresponding to the first point in time includes tumor accumulation regions 11a and biological accumulation regions 12a; the nuclear medicine data 10b corresponding to the second point in time includes tumor accumulation regions lib and biological accumulation regions 12b, the nuclear medicine data 10c corresponding to the third point in time includes tumor accumulation regions 11c and biological accumulation regions 12c; and the nuclear medicine data 10d corresponding to the fourth point in time includes tumor accumulation 11d and biological accumulation 12d.

In relation to the above, differences between the tumor accumulation and the biological accumulation will be explained, with reference to FIGS. 4 and 5. In FIG. 4, the curve 11 indicates temporal changes in a Standard Uptake Value (SUV) in the tumor accumulation parts in FIG. 3. Further, in FIG. 5, the curve 12 indicates temporal changes in the SUV in the biological accumulation parts in FIG. 3.

Figure 4:
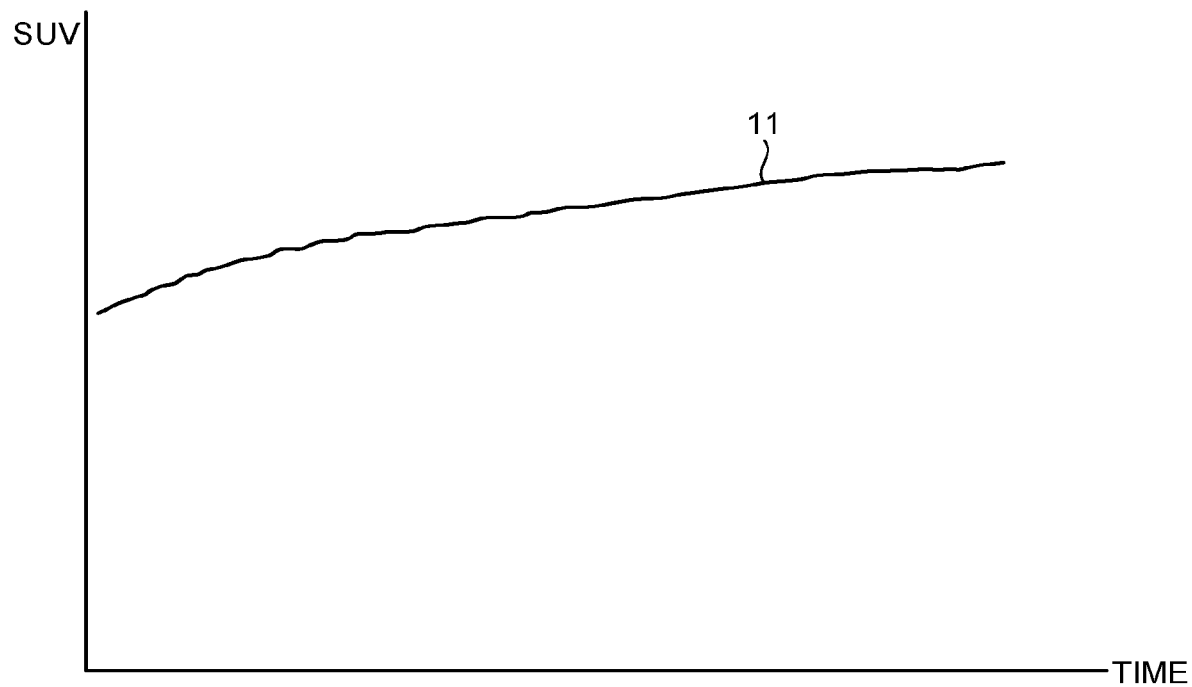
FIG. 4 is a chart for explaining a process according to the embodiment.
Figure 5:
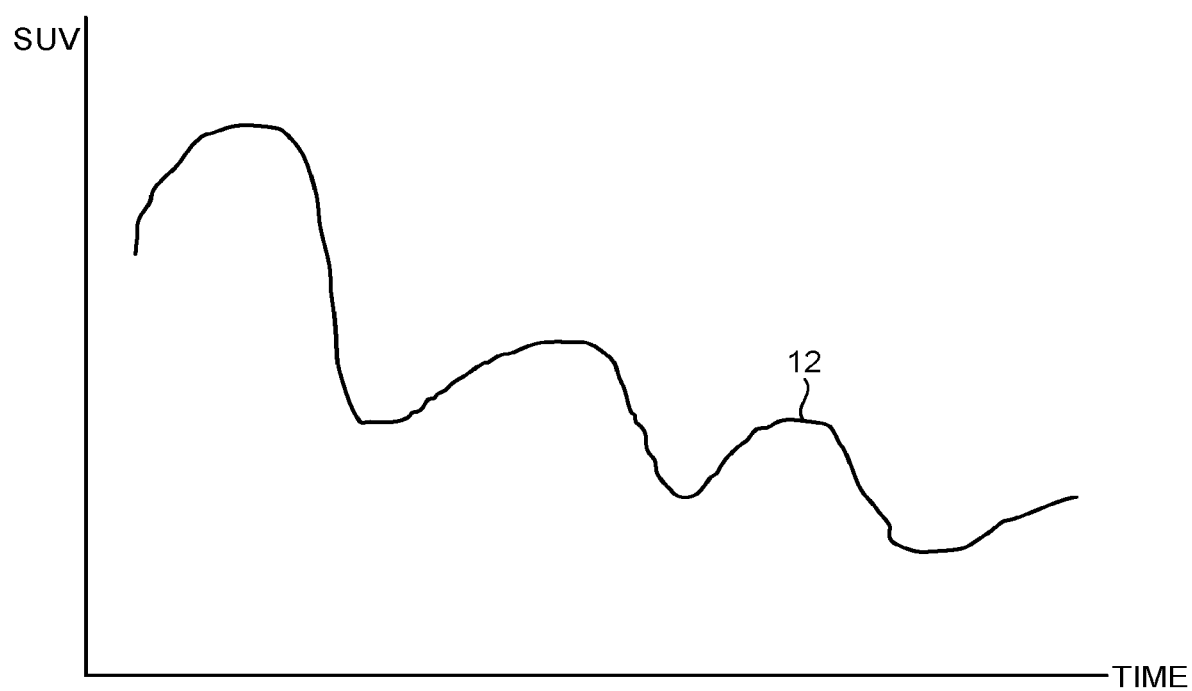
FIG. 5 is another chart for explaining a process according to the embodiment.

When FIGS. 4 and 5 are compared with each other, as illustrated in FIG. 4, the tumor accumulation has more gradual changes in the signal value than the biological accumulation does, so that the signal value changes on a longer-term time scale. In one example, in the tumor accumulation, the change rate of pixel values in a temporal change section can be explained with a change rate of drug-labeled isotopes caused by disintegration.

In contrast, as illustrated in FIG. 5, the biological accumulation has more abrupt changes in the signal value than the tumor accumulation does, so that the signal value changes on a shorter-term time scale, and the changes also tend to occur in an irregular manner. Accordingly, in the biological accumulation, the change rate of pixel values in a temporal change section cannot be explained only with a change rate of drug-labeled isotopes caused by disintegration. For example, the changes either last for a shorter period or are irregular. Further, spatially speaking, signal values keep appearing in relatively similar regions in the tumor accumulation, whereas the spatial regions in the biological accumulation where signal values appear tend to change in an irregular manner over the course of time. Consequently, by utilizing the notion that behaviors in how the signal values change are different between the tumor accumulation and the biological accumulation, the processing circuit 150 is able to distinguish the tumor accumulation and the biological accumulation from each other, while employing the identifying function 150c.

In one example, by employing the identifying function 150c, the processing circuit 150 is configured to identify a biological accumulation region, by comparing either an attenuation period or an increase period of the data values included in the first nuclear medicine data and the second nuclear medicine data with a threshold value. For example, when the time scale of the attenuation period or the increase period of the data values is on a shorter time scale than a predetermined threshold value determined as a time scale corresponding to tumor accumulation, the processing circuit 150 is configured, by employing the identifying function 150c, to identify that the data values are related to a biological accumulation region. Conversely, when the attenuation period or the increase period of the data values is on a longer time scale than the threshold value, the processing circuit 150 is configured to identify that the data values represent tumor accumulation. In another example, when the change rate of the data values exhibits a behavior that cannot be explained only with a change rate of drug-labeled isotopes caused by disintegration, the processing circuit 150 is configured, by employing the identifying function 150c, to identify that the data values are relevant to biological accumulation.

In yet another example, by employing the identifying function 150c, the processing circuit 150 is configured to identify a biological accumulation region, by comparing a matching degree of the data values included in the first nuclear medicine data and the second nuclear medicine data to a model waveform, with a threshold value. In an example, when the matching degree of the data values to the model waveform postulating tumor accumulation is lower than the threshold value, the processing circuit 150 is configured, by employing the identifying function 150c, to identify that the data values are related to a biological accumulation region. Conversely, when the matching degree of the data values to the model waveform is higher than the threshold value, the processing circuit 150 is configured, by employing the identifying function 150c, to identify that the data values represent tumor accumulation.

Further, by employing the identifying function 150c, the processing circuit 150 may be configured to calculate, with respect to each of the accumulation units included in a region of interest, a probability value indicating a probability of the accumulation being biological accumulation. Alternatively, by employing the identifying function 150c, the processing circuit 150 may be configured to calculate, with respect to each of the accumulation units included in a region of interest, a probability value indicating a probability of the accumulation being tumor accumulation.

Subsequently, at step S130, by employing the display controlling function 150i, the processing circuit 150 causes the display 120 serving as a display unit to display the identified biological accumulation regions. In an example, the processing circuit 150 causes the display 120 serving as the display unit to display the biological accumulation regions and the tumor accumulation regions that were identified so as to be marked with mutually-different colors.

Figure 6:
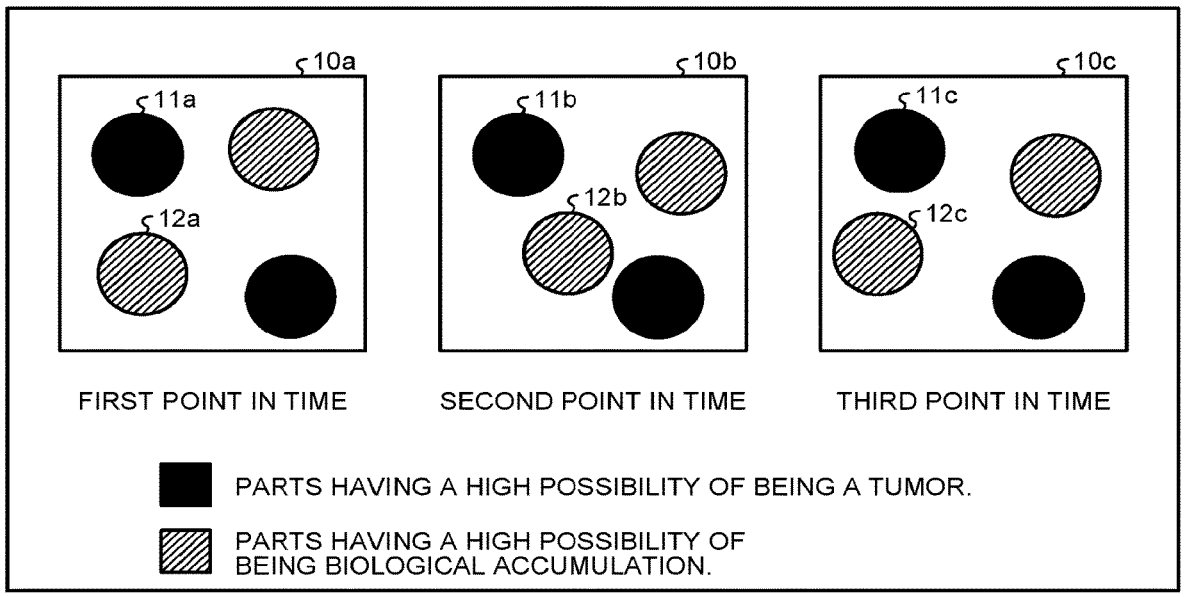
FIG. 6 is a drawing illustrating an example of a user interface related to the nuclear medicine diagnosis apparatus according to the first embodiment.

FIG. 6 illustrates an example of a user interface in this process. As illustrated in FIG. 6, by employing the display controlling function 150i, the processing circuit 150 is configured to extract, with respect to each of the time phases, the biological accumulation regions 12a, 12b, and 12c identified at step S120 and the tumor accumulation regions 11a, 11b, and 11c identified at step S120 and to further cause the display 120 serving as the display unit to display the extracted result. In an example, by employing the display controlling function 150i, the processing circuit 150 may be configured to cause the display 120 serving as the display unit to display the biological accumulation regions 12a, 12b, and 12c identified at step S120 and the tumor accumulation regions 11a, 11b, and 11c identified at step S120, so as to be marked with mutually-different colors while being kept in correspondence with the time phases.

As explained above, in the nuclear medicine diagnosis apparatus according to the first embodiment, the processing circuit 150 is configured to identify the biological accumulation regions on the basis of the time-divided nuclear medicine data and to further display, as necessary, the identified biological accumulation regions so as to be distinguished from the other regions. Consequently, the user is able to easily recognize the biological accumulation regions and the tumor accumulation regions visually, and thus usability is enhanced.

A Modification Example of First Embodiment

In a modification example of the present embodiment, for example, at a step between step S110 and step S120, the processing circuit 150 may, by employing the receiving function 150g, receive an input to select a region from the user. After the processing circuit 150 receives the input to select the region from the user by employing the receiving function 150g, the processing circuit 150 may identify, at step S130, a biological accumulation region included in the selected region, by employing the identifying function 150c.

Figure 8:
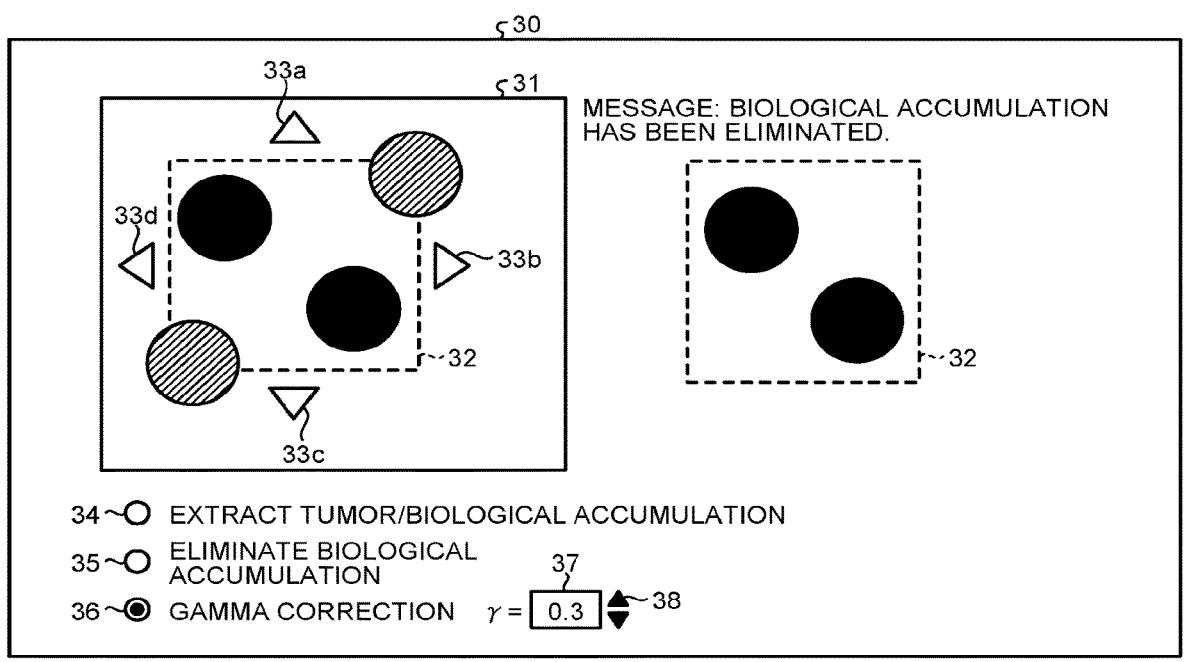
FIG. 8 is a drawing illustrating an example of a user interface related to a nuclear medicine diagnosis apparatus according to a modification example of the first embodiment, a fifth embodiment, and a sixth embodiment.

An example of a user interface in this process is illustrated in FIG. 8. In the example in FIG. 8, on a display screen 30, by employing the display controlling function 150i, the processing circuit 150 is configured to cause the display 120 to display an image 31 used for receiving a setting of a region of interest 32 from the user. As the image 31 used for receiving the setting of the region of interest 32 from the user, it is possible to use, for example, a still image, an image in a predetermined time phase, or a combined image generated from images in a plurality of time phases. Further, by employing the receiving function 150g, the processing circuit 150 is configured to receive a change in the setting of the region of interest 32, via buttons 33a, 33b, 33c, and 33d. Further, when the user selects a button 34, the processing circuit 150 is configured, by employing the identifying function 150c, to identify the biological accumulation regions and the tumor accumulation regions included in the region of interest 32 set at that point in time and is configured, by employing the display controlling function 150i, to cause the display 120 to display the biological accumulation regions and the tumor accumulation regions identified by using the user interface explained with reference to FIG. 6, for example.

In the modification example of the first embodiment, the user is able to freely set the region of interest and to automatically extract the biological accumulation regions with respect to the set region of interest. Consequently, usability is further enhanced, which makes it possible to reduce labor in diagnosing processes and to enhance precision levels of the diagnosing processes.

Second Embodiment

In the first embodiment, the example was explained in which, at step S120, the biological accumulation regions are identified on the basis of the temporal changes in the data values included in the first nuclear medicine data and the second nuclear medicine data which are the image data after the image reconstruction process is performed; however, possible embodiments are not limited to this example. In a second embodiment, at step S120, biological accumulation regions are identified on the basis of temporal changes in data values in first nuclear medicine data and second nuclear medicine data which are raw data (the data before the image reconstruction process is performed). In this situation, an example of the raw data may be the count information including the scintillator numbers (P), the energy values (E), and the detection times (T), for instance, and being obtained by the processing circuit 150 from the front end circuit 102 while employing the obtaining function 150a.

In the second embodiment, for example, at step S100, by employing the obtaining function 150a, the processing circuit 150 obtains, from the front end circuit 102, the raw data such as, for example, the count information including the scintillator numbers (P), the energy values (E), and the detection times (T). Subsequently, at step S110, by employing the dividing function 150b, the processing circuit 150 phase-divides the count information represented by the pieces of raw data and generates the first nuclear medicine data and the second nuclear medicine data. After that, at step S120, by employing the identifying function 150c, the processing circuit 150 identifies biological accumulation regions, on the basis of temporal changes in the data values included in the first nuclear medicine data and the second nuclear medicine data. In an example, by employing the identifying function 150c, the processing circuit 150 calculates difference data between the first nuclear medicine data and the second nuclear medicine data and identifies the biological accumulation regions on the basis of the magnitude of the difference data. In the first embodiment, the differences between the first nuclear medicine data and the second nuclear medicine data are in the pixel values. In contrast, in the second embodiment, the differences between the first nuclear medicine data and the second nuclear medicine data is merely presented as the difference data which is not pixel values. However, by comparing an attenuation period or an increase period of the difference data with a prescribed threshold value, it is possible to identify the biological accumulation regions similarly to the example in the first embodiment.

Third Embodiment

Possible embodiments are not limited to the examples described above. In a third embodiment, as a method for identifying biological accumulation, an example will be explained in which the biological accumulation identifying process at step S120 in FIG. 2 is performed by using a trained model trained through machine learning that uses a neural network. In other words, in the third embodiment, at step S120, the processing circuit 150 identifies the biological accumulation regions by employing the identifying function 150c, by inputting the first nuclear medicine data and the second nuclear medicine data obtained through the time-division, to the trained model generated through a learning process that uses a clinical image group kept in association with whether biological accumulation is present or absent.

In this situation, used as learning-purpose data of the neural network is, for example, the clinical image group obtained as a result of an image interpreter classifying whether biological accumulation is present or absent and sites. In other words, the processing circuit 150 is configured to use, as the learning data of the neural network, data serving as a piece of learning-purpose data in which a clinical image, information indicating the site in the clinical image, and information indicating whether or not the clinical image includes biological accumulation are kept in association with one another. For example, a piece of learning-purpose data used for the learning process may be information that keeps the following in association with one another: the site "large intestine" in a clinical image; data of the clinical image taken of the large intestine serving as the site corresponding to a plurality of time phases; and a flag "1" indicating that the clinical image includes biological accumulation. However, possible formats of the learning data used in the learning process according to the embodiment are not limited to the above example. In another example, for instance, a piece of learning-purpose data used for the learning process may be information that keeps the following in association with one another: the site "large intestine" in a clinical image; the clinical image taken of the large intestine serving as the site corresponding to a single time phase; and a flag "1" indicating that the clinical image includes biological accumulation. In yet another example, for instance, a piece of learning-purpose data used for the learning process may be information in which the data of the clinical image corresponding to a plurality of time phases is kept in association with information indicating whether or not the clinical image includes biological accumulation, while the learning data includes no information about the site. In yet another example, in place of the information indicating whether or not the clinical image includes biological accumulation, it is acceptable to use, as the learning-purpose data, information indicating the type of accumulation included in the clinical image, such as information indicating "1" for biological accumulation and indicating "2" for tumor accumulation.

As explained above, at the time of executing the learning process, the processing circuit 150 is configured, by employing the learning function 150j, to generate the trained model with the implementation of the machine learning by inputting, to the neural network, a plurality of pieces of data in each of which, for example, the following are kept in association with one another: the data of a clinical image corresponding to a plurality of time phases; the information indicating the site in the clinical image; and the information indicating whether or not the clinical image includes biological accumulation.

Subsequently, at step S120 at the time of implementing the trained model, the processing circuit 150 determines, by employing the identifying function 150c, whether biological accumulation is present or absent in an image to be interpreted and a site therein, by inputting the first nuclear medicine data and the second nuclear medical data obtained through the time-division to the trained model. For example, when the trained model outputs "1" as a value indicating whether biological accumulation is present or absent, the processing circuit 150 determines, by employing the identifying function 150c, that the image to be interpreted includes biological accumulation. In contrast, for example, when the trained model outputs a real number value between 0 and 1 indicating a probability of the region of interest including biological accumulation, the processing circuit 150 determines, by employing the identifying function 150c, that the probability of the image to be interpreted including biological accumulation is the real number value. In another example, when the trained model is configured to output 0, 1, or 2, the processing circuit 150 determines, by employing the identifying function 150c, that no accumulation is included when the output result is 0, that biological accumulation is included when the output result is 1, and that tumor accumulation is present when the output result is 2.

As explained above, in the third embodiment, the biological accumulation is determined by using the neural network. Consequently, it is possible to enhance the precision level of the biological accumulation identifying process, and usability is thus further enhanced.

Fourth Embodiment

Possible embodiments are not limited to the above examples. In a fourth embodiment, an example will be explained in which, in response to a request from the user, the processing circuit 150 is configured, by employing the display controlling function 150i, to cause the display 120 to additionally display, with respect to a region having a possibility of being a biological accumulation site, information serving as a reason or a judgment basis as to whether or not the region is a biological accumulation site. In an example, the processing circuit 150 is configured to receive an input to select a region from the user by employing the receiving function 150g and is configured to cause the display 120 serving as the display unit to display data in a plurality of time phases related to the region by employing the display controlling function 150i.

Figure 7:
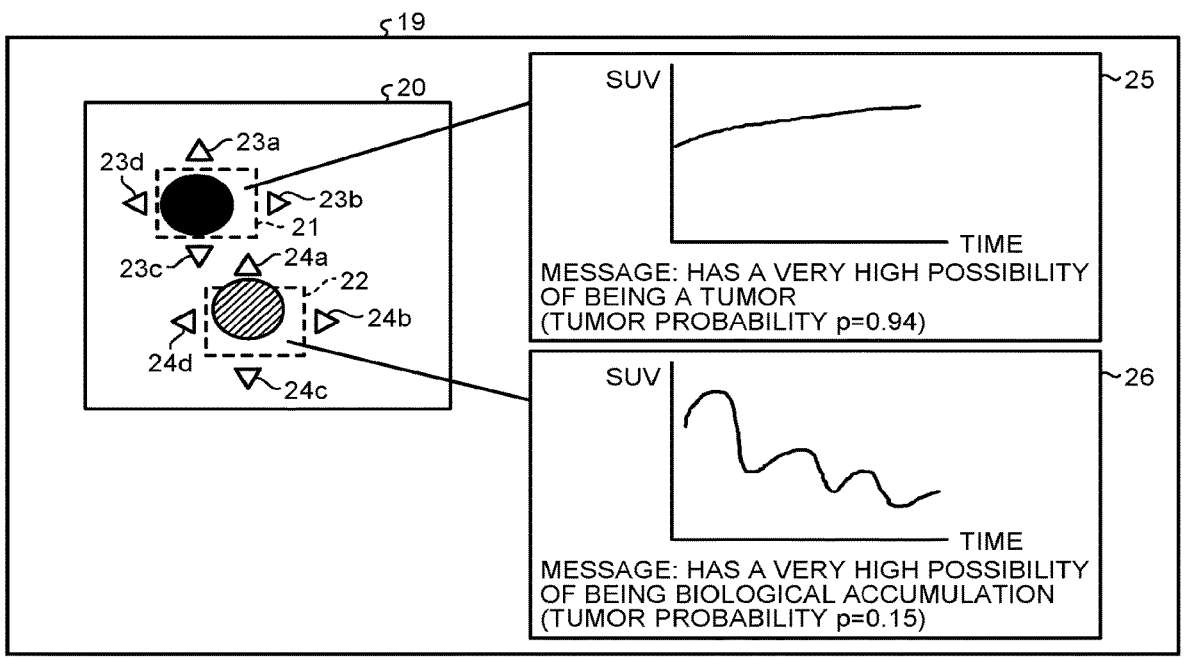
FIG. 7 is a drawing illustrating an example of a user interface related to a nuclear medicine diagnosis apparatus according to a fourth embodiment.

An example of a user interface in this process is illustrated in FIG. 7. By employing the display controlling function 150i, the processing circuit 150 is configured to cause the display 120 to display, on a display screen 19, an image 20 used for receiving settings of regions of interest 21 and 22 from the user. As the image 20 used for receiving the settings of the region of interest 21 and the like from the user, it is possible to use, for example, a still image, an image in a predetermined time phase, or a combined image generated from images in a plurality of time phases. Further, by employing the receiving function 150g, the processing circuit 150 is configured to receive changes in the setting of the region of interest 21, via buttons 23a, 23b, 23c, and 23d. Similarly, by employing the receiving function 150g, the processing circuit 150 is configured to receive changes in the setting of the region of interest 22, via buttons 24a, 24b, 24c, and 24d.

In this situation, for example, when the user clicks on the region of interest 21, the processing circuit 150 is configured to cause the display 120 serving as the display unit to display supplemental information 25, by employing the display controlling function 150i. In an example, when the user clicks on the region of interest 21, the processing circuit 150 causes the display 120 serving as the display unit to display data in a plurality of time phases related to the region of interest 21, as the supplemental information 25, by employing the display controlling function 150i. In this situation, the data in the plurality of time phases related to the region of interest 21 may be data indicating an average value of signal values within the region of interest 21 with respect to each of a plurality of points in times or may be data indicating a signal value at a single point within the region of interest 21 with respect to each of a plurality of points in times.

Further, by employing the display controlling function 150i, the processing circuit 150 may cause the display 120 serving as the display unit to display information indicating whether or not a signal present in the region of interest 21 originates from biological accumulation, as the supplemental information 25. For example, at step S120, when the processing circuit 150 determines, by employing the identifying function 150c, that the region of interest 21 has a very high possibility of being biological accumulation, the processing circuit 150 causes, by employing the display controlling function 150i, the display 120 serving as the display unit to display a message indicating that the data present in the region of interest has a very high possibility of being biological accumulation, as the supplemental information 25. Conversely, in another example, at step S120, when the processing circuit 150 determines, by employing the identifying function 150c, that the region of interest 21 has a very high possibility of being tumor accumulation, the processing circuit 150 causes, by employing the display controlling function 150i, the display 120 serving as the display unit to display a message indicating that the data present in the region of interest has a very high possibility of being tumor accumulation, as the supplemental information 25.

In yet another example, at step S120, by employing the display controlling function 150i, when the processing circuit 150 calculates a probability that a signal present in the region of interest may be tumor accumulation or a probability that the signal may be biological accumulation, the processing circuit 150 may cause, by employing the display controlling function 150i, the display 120 serving as the display unit to display the probability as the supplemental information 25.

Further, similarly, when the user clicks on the region of interest 22, the processing circuit 150 causes, by employing the display controlling function 150i, the display 120 serving as the display unit to display data in the plurality of time phases related to the region of interest 22 or the like, as supplemental information 26.

As explained above, in the fourth embodiment, when the user selects the region of interest 21, 22, the processing circuit 150 is configured, by employing the display controlling function 150i, to cause the display 120 serving as the display unit to display the supplemental information 25, 26 that serves as a judgment basis as to whether the region of interest is biological accumulation or tumor accumulation. Consequently, the user is able to make judgment more accurately as to whether the signal values related to the regions of interest originate from biological accumulation or tumor accumulation. Usability is thus enhanced, and it is possible to further reduce the labor in diagnosing processes and to further enhance precision levels of the diagnosing processes.

Fifth Embodiment

In a fifth embodiment, when biological accumulation is identified on the basis of any of the embodiments described above, a corrected image obtained by eliminating the biological accumulation from the image is provided for the user. In other words, by employing the image generating function 150*h*, the processing circuit 150 is configured to generate third nuclear medicine data obtained by correcting pixel values in the site determined to be a biological accumulation region, on the basis of the biological accumulation region identified by the identifying function 150*c*. In this situation, correcting the pixel values in the site determined to be a biological accumulation region denotes, for example, changing the pixel values in the site determined to be a biological accumulation region to 0s or replacing those pixel values with an average value of the pixel values in the surroundings thereof.

An example of a user interface in this process is illustrated in FIG. 8. In FIG. 8, when the user clicks on a button 35, the processing circuit 150 is configured, by employing the image generating function 150*h*, to generate the third nuclear medicine data obtained by correcting the pixel values in the site determined to be a biological accumulation region within a region of interest 32. For example, by employing the image generating function 150*h*, the processing circuit 150 is configured to generate the third nuclear medicine data obtained by replacing the pixel values in the site determined to be a biological accumulation region within the region of interest, with 0s. Subsequently, by employing the display controlling function 150*i*, the processing circuit 150 is configured to cause the display 120 serving as the display unit to display the generated third nuclear medicine data, as illustrated in the right section of FIG. 8, for example.

As explained above, in the fifth embodiment, it is possible to display the image from which the biological accumulation region is eliminated. Consequently, it is possible to further reduce the labor in diagnosing processes and to further enhance precision levels of the diagnosing processes.

Sixth Embodiment

In a six embodiment, a gamma correction is performed on a biological accumulation site in a reconstructed image, to make it easier to check to see whether or not the biological accumulation site includes tumor accumulation.

In this situation, the gamma correction is a non-linear transformation characterized with a parameter γ. More specifically, the gamma correction is a transformation expressed as $V_{out}=A\, V^{\gamma}_{in}$, where $V_{in}$ denotes an input pixel value, A denotes a constant, and $V_{out}$ denotes an output pixel value and is an example of a transformation capable of visually emphasizing differences in the pixel values. Consequently, when a biological accumulation site includes tumor accumulation, it is possible to discover the tumor accumulation more easily as a result of the user performing the gamma transformation on the reconstructed image.

An example of a user interface in this process is illustrated in FIG. 8. When the user selects a button 36, the processing circuit 150 is configured, by employing the image generating function 150*h*, to generate fourth nuclear medicine data obtained by performing the gamma correction characterized with the parameter γ input to an input field 37, on a biological accumulation region identified by the identifying function 150*c*. It is possible to change the value of the parameter γ, by using a button 38 or the like, for example.

As explained above, in the sixth embodiment, the input for performing the gamma correction is received from the user. As a result, the user is able to easily check to see whether or not the biological accumulation site includes tumor accumulation. Consequently, it is possible to further reduce the labor in diagnosing processes and to further enhance precision levels of the diagnosing processes.

According to at least one aspect of the embodiments described above, it is possible to enhance usability.

In relation to the embodiments described above, the following notes are disclosed as certain aspects and selective characteristics of the present disclosure.

Note 1:

A nuclear medicine diagnosis apparatus provided in one aspect of the present disclosure includes an obtaining unit, a dividing unit, and an identifying unit. The obtaining unit is configured to obtain nuclear medicine data. The dividing unit is configured to time-divide the nuclear medicine data into at least first nuclear medicine data and second nuclear medicine data. The identifying unit is configured to identify a biological accumulation region on the basis of a temporal change in data values included in the first nuclear medicine data and the second nuclear medicine data.

Note 2:

The following may further be provided:
  a receiving unit configured to receive an input to select a region from a user; and
  a display controlling unit configured to cause a display unit to display data in a plurality of time phases related to the region.

Note 3:

A receiving unit configured to receive an input to select a region from a user may further be provided, so that when the receiving unit receives the input to select the region from the user, the identifying unit identifies the biological accumulation region included in the region.

Note 4:

An image generating unit may further be provided, the image generating unit being configured, on the basis of the biological accumulation region identified by the identifying unit, to generate third nuclear medicine data obtained by correcting pixel values in a site determined to be the biological accumulation region.

Note 5:

The identifying unit may be configured to identify the biological accumulation region, by inputting the first nuclear medicine data and the second nuclear medicine data to a trained model generated through a learning process that uses a clinical image group kept in association with whether biological accumulation is present or absent.

Note 6:

An image generating unit may further be provided, the image generating unit being configured to generate fourth nuclear medicine data obtained by performing a gamma correction on the biological accumulation region identified by the identifying unit.

Note 7:

The identifying unit may be configured to identify the biological accumulation region by comparing an attenuation period of the data values with a threshold value or by comparing a matching degree of the data values to a model waveform with a threshold value.

Note 8:

The identifying unit may be configured to identify that the data values are related to the biological accumulation region when a time scale of an attenuation period or an increase period of the data values is on a shorter time scale than a predetermined threshold value determined as a time scale corresponding to tumor accumulation.

Note 9:

The identifying unit may be configured to identify that the data values are relevant to biological accumulation, when a change rate of the data values exhibits a behavior that cannot be explained only with a change rate of drug-labeled isotopes caused by disintegration.

Note 10:

The identifying unit may be configured to identify that the data values are related to the biological accumulation region, when a matching degree of the data values to a model waveform postulating tumor accumulation is lower than a threshold value.

Note 11:

A data processing method provided according to at least one aspect of the present disclosure includes:
  obtaining nuclear medicine data;
  time-dividing the nuclear medicine data into at least first nuclear medicine data and second nuclear medicine data; and
  identifying a biological accumulation region, on the basis of a temporal change in data values included in the first nuclear medicine data and the second nuclear medicine data.

Note 12:

A data processing method provided according to at least one aspect of the present disclosure causes a computer to perform:
  obtaining nuclear medicine data;
  time-dividing the nuclear medicine data into at least first nuclear medicine data and second nuclear medicine data; and
  identifying a biological accumulation region, on the basis of a temporal change in data values included in the first nuclear medicine data and the second nuclear medicine data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnosis apparatus, comprising:
  a processing circuit configured to:
    obtain nuclear medicine data;
    time-divide the nuclear medicine data into at least first nuclear medicine data and second nuclear medicine data; and
    identify a biological accumulation region, based on a basis of a temporal change in data values included in the first nuclear medicine data and the second nuclear medicine data,
  wherein the processing circuit is further configured to identify the biological accumulation region by comparing an attenuation period of the data values with a first threshold value or by comparing a matching degree of the data values to a model waveform with a second threshold value, the attenuation period being a time period during which the data values are attenuated.

2. The nuclear medicine diagnosis apparatus according to claim 1, wherein
  the processing circuit is further configured to receive an input to select a region from a user, and
  the processing circuit is further configured to cause a display to display data in a plurality of time phases related to the selected region.

3. The nuclear medicine diagnosis apparatus according to claim 1, wherein
  the processing circuit is further configured to receive an input to select a region from a user, and
  upon receipt of the input to select the region from the user, the processing circuit is further configured to identify the biological accumulation region included in the selected region.

4. The nuclear medicine diagnosis apparatus according to claim 1, wherein, based on the biological accumulation region, the processing circuit is further configured to generate third nuclear medicine data obtained by correcting pixel values in a site determined to be the biological accumulation region.

5. The nuclear medicine diagnosis apparatus according to claim 1, wherein the processing circuit is further configured to identify the biological accumulation region, by inputting the first nuclear medicine data and the second nuclear medicine data to a trained model generated through a learning process that uses a clinical image group kept in association with whether biological accumulation is present or absent.

6. The nuclear medicine diagnosis apparatus according to claim 1, wherein the processing circuit is further configured to generate fourth nuclear medicine data obtained by performing a gamma correction on the biological accumulation region.

7. A data processing method, comprising:
  obtaining nuclear medicine data;
  time-dividing the nuclear medicine data into first nuclear medicine data and second nuclear medicine data; and
  identifying a biological accumulation region, based on a temporal change in data values included in the first nuclear medicine data and the second nuclear medicine data,
  wherein the method further comprises identifying the biological accumulation region by comparing an attenuation period of the data values with a first threshold value or by comparing a matching degree of the data values to a model waveform with a second threshold value, the attenuation period being a time period during which the data values are attenuated.

8. A computer program product having a non-transitory computer-readable medium including programmed instructions, wherein the instructions, when executed by a computer, cause the computer to perform:
  obtaining nuclear medicine data;
  time-dividing the nuclear medicine data into at least first nuclear medicine data and second nuclear medicine data; and
  identifying a biological accumulation region, based on a temporal change in data values included in the first nuclear medicine data and the second nuclear medicine data,
  wherein the instructions, when executed by the computer, cause the computer to further perform identifying the biological accumulation region by comparing an attenuation period of the data values with a first threshold value or by comparing a matching degree of the data values to a model waveform with a second threshold value, the attenuation period being a time period during which the data values are attenuated.

* * * * *